United States Patent
Matsunami et al.

(10) Patent No.: US 9,885,602 B2
(45) Date of Patent: Feb. 6, 2018

(54) PARTICLE SENSOR

(71) Applicant: PANASONIC INTELLECTUAL PROPERTY MANAGEMENT CO., LTD., Osaka (JP)

(72) Inventors: Hirotaka Matsunami, Osaka (JP); Shintaro Hayashi, Hyogo (JP); Shinichi Kitaoka, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/388,614

(22) Filed: Dec. 22, 2016

(65) Prior Publication Data

US 2017/0184447 A1 Jun. 29, 2017

(30) Foreign Application Priority Data

Dec. 28, 2015 (JP) .................................. 2015-257505

(51) Int. Cl.
| | |
|---|---|
| *G01N 21/00* | (2006.01) |
| *G01J 1/02* | (2006.01) |
| *G01J 1/04* | (2006.01) |
| *G01N 21/53* | (2006.01) |
| *G01N 15/00* | (2006.01) |
| *G08B 17/107* | (2006.01) |

(52) U.S. Cl.
CPC ........... *G01J 1/0252* (2013.01); *G01J 1/0403* (2013.01); *G01N 15/00* (2013.01); *G01N 21/53* (2013.01); *G08B 17/107* (2013.01)

(58) Field of Classification Search
CPC ...... G02B 1/041; G02B 1/04; G02B 13/0085; G02B 5/223; G02B 3/0031; G02B 3/00; G02B 5/208; G02B 13/006; G02B 17/0647; G02B 26/001; G02B 27/0043; G02B 5/08; G02B 5/0816; G02B 5/0891; G02B 5/22
See application file for complete search history.

(56) References Cited

U.S. PATENT DOCUMENTS

| | | |
|---|---|---|
| 4,241,282 A | 12/1980 | Tresch et al. |
| 2015/0346081 A1* | 12/2015 | Howard ............. G01N 15/0227 356/246 |

FOREIGN PATENT DOCUMENTS

| | | |
|---|---|---|
| JP | 58-52269 | 11/1983 |
| JP | 62-211979 | 9/1987 |
| JP | 6-43386 | 2/1994 |

(Continued)

*Primary Examiner* — Michael P Stafira
(74) *Attorney, Agent, or Firm* — Greenblum & Bernstein, P.L.C.

(57) ABSTRACT

A particle sensor is provided. The particle sensor includes a light projector that projects light to a detection area. A light receiver receives scattered light. The scattered light is light from the light projector that has been scattered by particles in the detection area. A first support supports the light receiver. A second support supports the light projector and has a linear expansion coefficient different from a linear expansion coefficient of the first support. The first support includes a first placement region in which the light receiver is disposed and a second placement region in which the second support is disposed. The first placement region and the second placement region are located at different distances from at least one of an optical axis of the light projector and an optical axis of the light receiver.

20 Claims, 8 Drawing Sheets

(56) References Cited

FOREIGN PATENT DOCUMENTS

| | | |
|---|---|---|
| JP | 9-32830 | 2/1997 |
| JP | 2902491 | 3/1999 |
| JP | 11-248629 | 9/1999 |
| JP | 2006-189337 | 7/2006 |
| JP | 2007-208065 | 8/2007 |

\* cited by examiner

PARTICLE SENSOR

CROSS REFERENCE TO RELATED APPLICATION

This application claims the benefit of priority of Japanese Patent Application Number 2015-257505 filed on Dec. 28, 2015, the entire content of which is hereby incorporated by reference.

BACKGROUND

1. Technical Field

The present disclosure relates to a particle sensor.

2. Description of the Related Art

Known particle sensors include a scattered light particle sensor that uses scattered light to detect airborne particles.

A scattered light particle sensor is a photoelectric sensor including a light projector and a light receiver, and emits light via the light projector into gas introduced into the sensor as a target to be measured and detects particles in the gas by detecting light scattered by the particles (for example, see Japanese Unexamined Patent Application Publication No. H11-248629). With this, airborne dust, pollen, smoke, and PM 2.5 (fine particulate matter), for example, can be detected.

SUMMARY

Semiconductor light emitters such as semiconductor lasers are used as the light projectors in particle sensors. The semiconductor light emitter itself generates heat as a result of emitting light. This increases the temperature and reduces light output of the semiconductor light emitter. In other words, the heat generated by the semiconductor light emitter itself reduces the light output of the semiconductor light emitter.

As a result, in particle sensors that use a semiconductor light emitter as the light projector, the detection accuracy decreases as the light emitting time of the light projector increases, leading to a problem of variations in detection accuracy.

In this case, it is conceivable to correct for the changes in light output caused by changes in temperature of the light projector by installing a circuit that imparts gain to counteract the changes in light output caused by the changes in temperature of the light projector. However, correcting for the changes in light output using a circuit increases costs.

The present disclosure has been made in view of the above problem, and has an object to provide a particle sensor capable of inhibiting variations in detection accuracy resulting from changes in light output caused by changes in temperature of the light projector at low cost.

In order to achieve the above object, in one aspect, the particle sensor according to the present disclosure includes: a light projector that projects light to a detection area; a light receiver that receives scattered light, the scattered light being light from the light projector that has been scattered by particles in the detection area; a first support that supports the light receiver; and a second support that supports the light projector and has a linear expansion coefficient different from a linear expansion coefficient of the first support. The first support includes a first placement region in which the light receiver is disposed and a second placement region in which the second support is disposed. The first placement region and the second placement region are located at different distances from at least one of an optical axis of the light projector and an optical axis of the light receiver.

According to the present disclosure, variations in detection accuracy resulting from changes in light output caused by changes in temperature of the light projector can be inhibited at low cost.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF THE EMBODIMENT

Hereinafter, an embodiment according to the present disclosure will be described with reference to the drawings. Note that the embodiment described below shows a specific example of the present disclosure. The numerical values, shapes, materials, elements, the arrangement and connection of the elements, etc., indicated in the following embodiment are mere examples, and therefore are not intended to limit the inventive concept. Therefore, among the elements in the following embodiment, those not recited in any of the independent claims defining the most generic part of the inventive concept are described as optional elements.

Note that the respective figures are schematic diagrams and are not necessarily precise illustrations. Additionally, like reference signs indicate like elements. As such, overlapping explanations of like elements are omitted or simplified.

Moreover, in the description and figures, the X, Y, and Z axes refer to the three axes of the three dimensional coordinate system, where vertical directions correspond to the Z axis, and directions perpendicular to the Z axis (directions parallel to the XY plane) correspond to horizontal directions.

Embodiment

Figure 1:
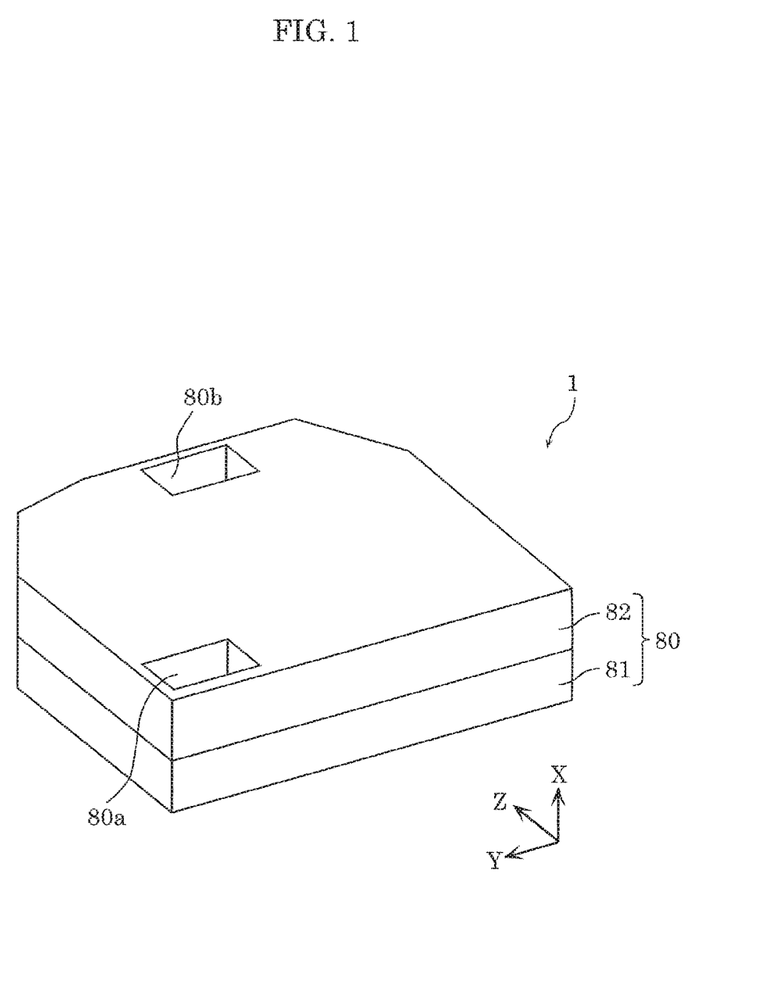
FIG. 1 is an external perspective view of a particle sensor according to an embodiment.
Figure 2:
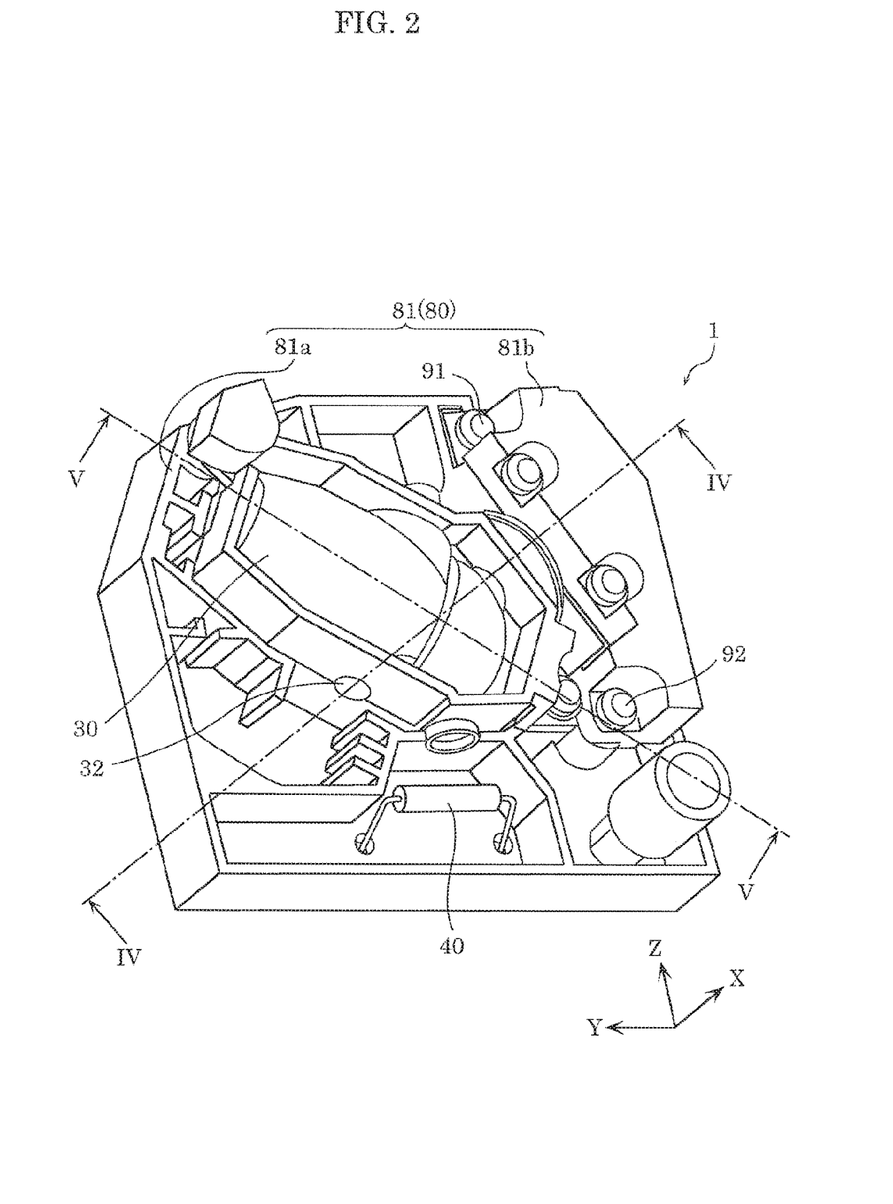
FIG. 2 is a perspective view of the particle sensor according to the embodiment with a first housing removed.
Figure 3:
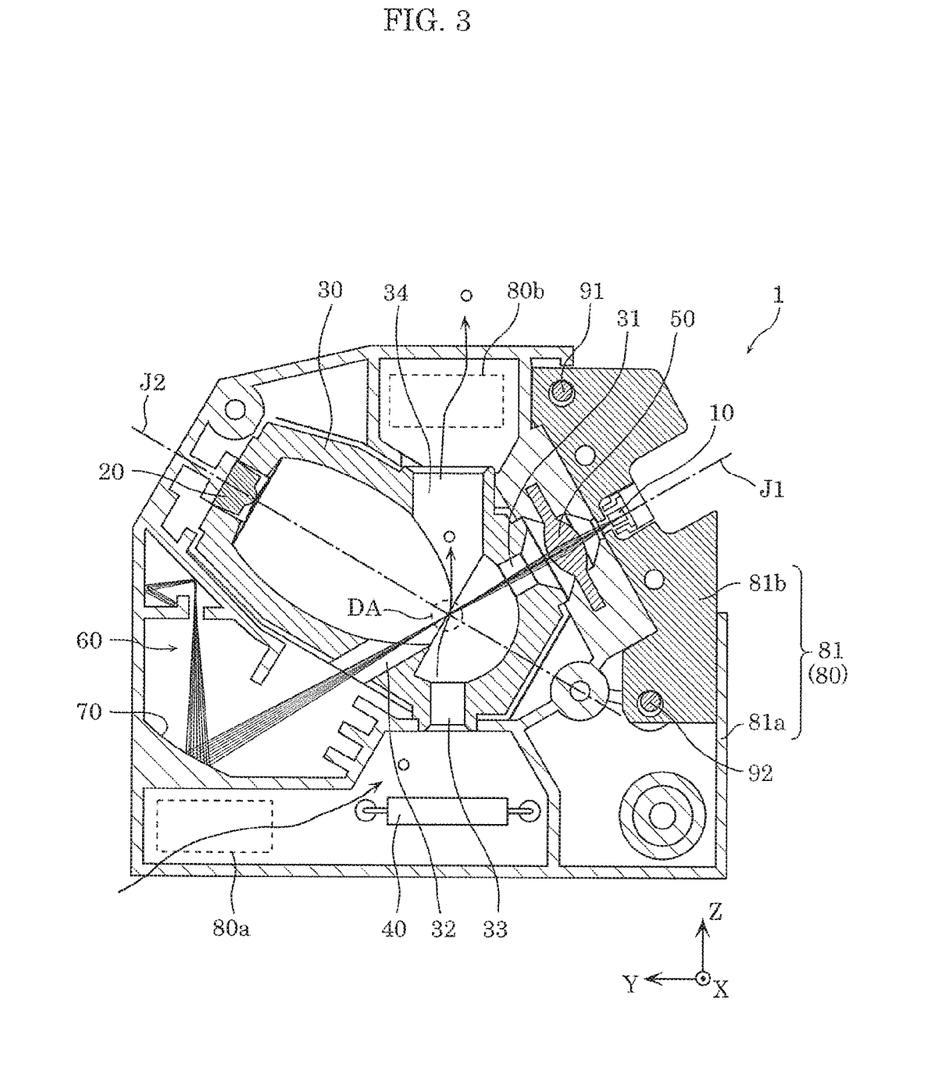
FIG. 3 is a cross sectional view (in the YZ plane) of the particle sensor according to the embodiment.
Figure 4:
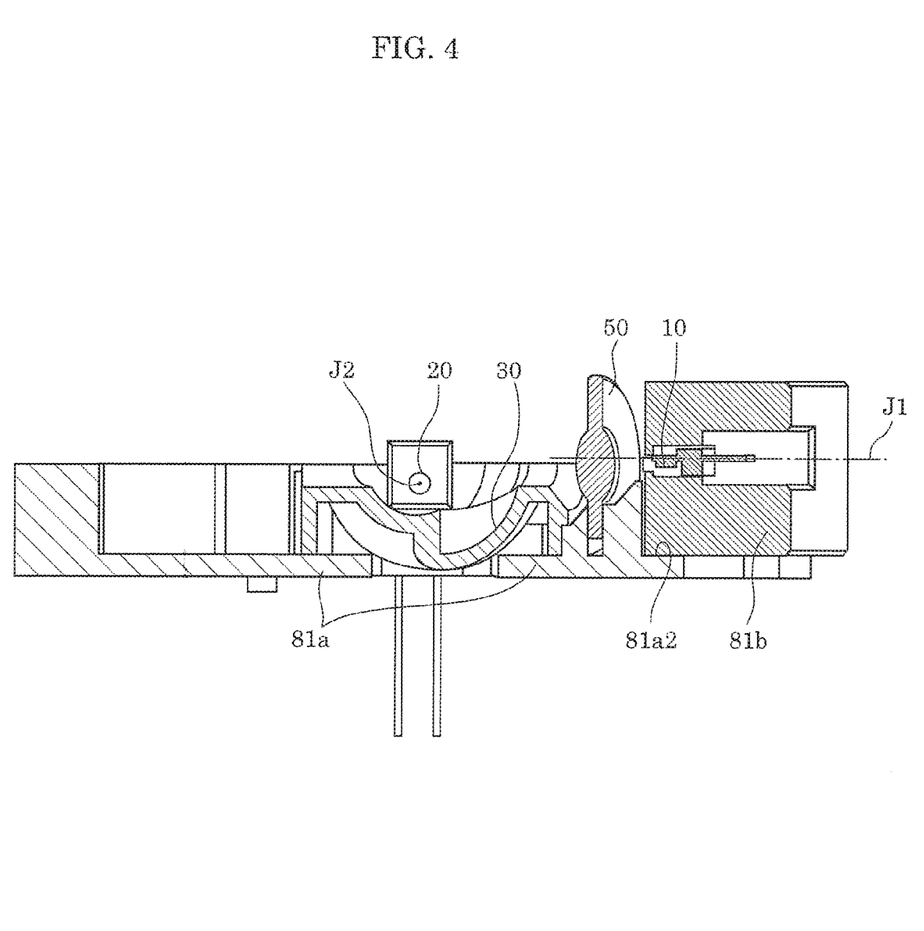
FIG. 4 is a cross sectional view (in the XY plane taken along line IV-IV in FIG. 2) of the particle sensor according to the embodiment.
Figure 5:
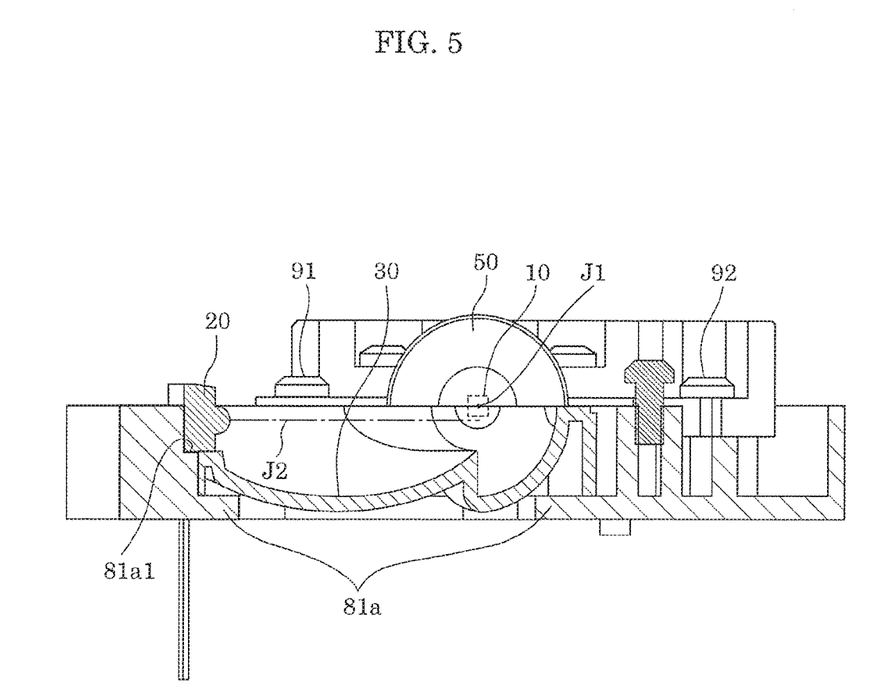
FIG. 5 is a cross sectional view (in the XY plane taken along line V-V in FIG. 2) of the particle sensor according to the embodiment.

Particle sensor 1 according to this embodiment will be described with reference to FIG. 1 through FIG. 5. FIG. 1 is an external perspective view of particle sensor 1 according to this embodiment. FIG. 2 is a perspective view of particle sensor 1 with first housing 81 removed. FIG. 3 through FIG. 5 are cross sectional views of particle sensor 1. FIG. 3 is a cross section in the YZ plane. FIG. 4 is a cross section in the XY plane taken along line IV-IV in FIG. 2. FIG. 5 is a cross section in the XY plane taken along line V-V in FIG. 2. Note that FIG. 3 shows traces of light beams emitted by light projector 10.

As illustrated in FIG. 3 and FIG. 4, particle sensor 1 is a photoelectric sensor that includes light projector 10 and light receiver 20, and detects airborne particles as a result of light receiver 20 receiving light that has been emitted by light projector 10 and scattered by particles in detection area DA. Particles targeted for detection by particle sensor 1 include, for example, dust, pollen, smoke, and PM2.5 that are 2 micrometers or finer. Particle sensor 1 can detect, for example, the presence or absence of particles, the number of particles, particle size, and particle concentration.

As illustrated in FIG. 2 through FIG. 4, particle sensor 1 includes light projector 10, light receiver 20, first reflector 30, heater 40, projection lens 50, light attenuator 60, and second reflector 70.

As illustrated in FIG. 1 through FIG. 4, particle sensor 1 includes housing 80 in which light projector 10, light receiver 20, first reflector 30, heater 40, projection lens 50, light attenuator 60, and second reflector 70 are housed. Note that, as illustrated in FIG. 3, light projector 10 and light receiver 20 are disposed in housing 80 such that their respective optical axes intersect in detection area DA.

Detection area DA is an aerosol detection area for detecting particles (aerosol) dispersed in the gas to be measured. Detection area DA is also a scattered light region in which scattered light, which is light scattered by particles dispersed in gas, formed. In other words, in detection area DA, light emitted by light projector 10 is reflected off particles dispersed in gas, resulting in scattered light. In this embodiment, detection area DA includes an area in which optical axis J1 of light projector 10 and optical axis J2 of light receiver 20 intersect in a plan view, and is in a path along which particles in the interior of first reflector 30 travel. Detection area DA is, for example, 2 millimeters in diameter. As illustrated in FIG. 1 and FIG. 3, the gas to be measured enters via inlet 80a of housing 80, travels through detection area DA, and then exits through outlet 80b.

Light projector 10 projects light to detection area DA. Light projector 10 is a light source that emits light of a predetermined wavelength, and is a light emitter that emits, for example, infrared light, blue light, green light, red light, or ultraviolet light. A semiconductor light emitter such as an LED or LD (semiconductor laser) may be used as light projector 10. A red light LD that emits red light may be used as a low cost, high output light projector 10. Moreover, light projector 10 may be configured to emit mixed waves of two or more wavelengths. In this embodiment, optical axis J1 of light projector 10, for example, passes through detection area DA.

Figure 6:
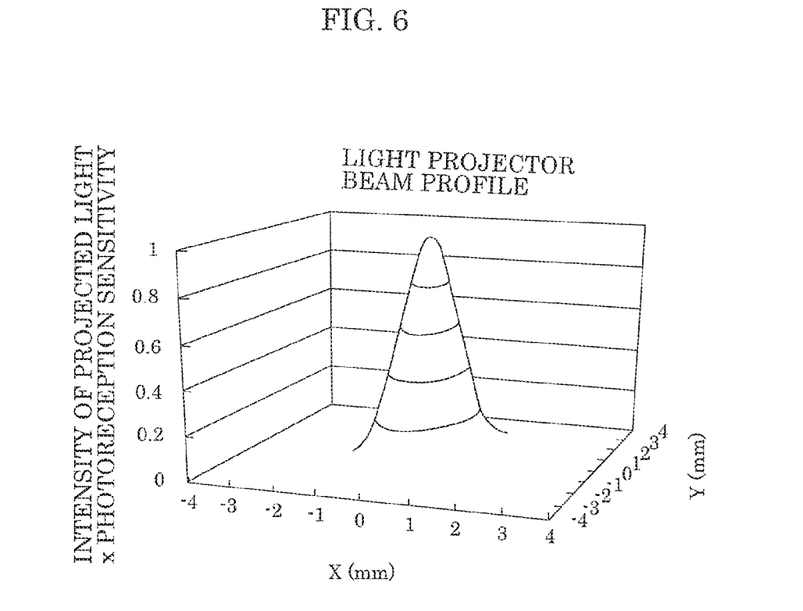
FIG. 6 illustrates one example of a beam profile of a light projector in the particle sensor according to the embodiment.

As one example, light projector 10 emits light having the intensity distribution shown in FIG. 6. FIG. 6 illustrates one example of a beam profile of light projector 10. As illustrated in FIG. 6, the intensity distribution in any given cross section of the light emitted by light projector 10 is a Gaussian distribution. Note that if at least a portion of the intensity changes, the intensity distribution of the light emitted by light projector 10 is not limited to the distribution illustrated in FIG. 6.

Note that the shorter the wavelength of light emitted by light projector 10 is, the easier it is to detect small diameter particles. Moreover, the method of controlling the emission of light by light projector 10 is not limited to a particular method; light emitted by light projector 10 may be continuous or pulsed light achieved by driving light projector 10 with direct current. Moreover, the output magnitude of light projector 10 may be temporally adjusted.

Light receiver 20 is a photodetector that receives light from light projector 10 that has been dispersed by particles dispersed in gas in detection area DA. In other words, light receiver 20 receives light that has been emitted by light projector 10 and reflected and scattered by particles in detection area DA. Light receiver 20 is a device that converts received light into an electric signal, such as a photodiode, photo IC diode, phototransistor, or a photomultiplier tube.

First reflector 30 reflects and guides, to light receiver 20, light from light projector 10 that has been scattered by particles in detection area DA. In this embodiment, first reflector 30 is a condensing mirror that reflects, guides, and focuses onto light receiver 20 light scattered by particles in detection area DA.

More specifically, as illustrated in FIG. 3, first reflector 30 is an elliptical mirror whose inner surface (reflective surface) forms a segment of a spheroid (ellipsoid of revolution). The inner surface of first reflector 30 has a cross sectional shape of a segment of an ellipse. In this case, among the two focal points that define the ellipse of the spheroid formed by the inner surface of first reflector 30, one (the first focal point) is, for example, located in detection area DA, and the other (the second focal point) is, for example, located in the vicinity of light receiver 20 (for example, in the center of light receiver 20).

With this, light scattered by particles in detection area DA can strike light receiver 20 after reflecting only a low number of times (one time or several times). In other words, the attenuation of light due to the light reflecting many times can be avoided. This increases the light reception efficiency of light receiver 20 and thus increases particle detection efficiency. Note that the ellipse included of the spheroid defined by the shape of the inner surface of first reflector 30 has, for example, a major axis of 20 millimeters to 100 millimeters, and a minor axis of 10 millimeters to 50 millimeters.

The inner surface of first reflector 30 is a reflective surface, and, for example, may be a surface that is unlikely to scatter light and is low in absorptivity and high in reflectivity (e.g., a specular surface). With this, the majority of light incident on first reflector 30 can be guided to light receiver 20. First reflector 30 may include, for example, metal as a base material such that the inner surface thereof is itself a reflective surface, and, alternatively, may include resin or metal as a base material and a reflective film formed on the inner surface as the reflective surface. The reflective film may be a reflective metal film of, for example, aluminum, gold, silver, or copper, a specular film, or a dielectric multilayer film. More specifically, silver plating or aluminum vapor-deposited film may be used as the reflective film. Forming such a reflective film increases the reflectivity of the inner surface of first reflector 30.

First reflector 30 includes light entrance aperture 31 for introducing light from light projector 10 into the interior of first reflector 30, and light exit aperture 32 through which light exits first reflector 30. Light entrance aperture 31 is a through-hole for light from outside first reflector 30 to enter into the interior of first reflector 30, and light exit aperture 32 is a through-hole for light from the interior of first reflector 30 to exit out of first reflector 30. Light entrance aperture 31 and light exit aperture 32 are exemplified as, but not limited to, cylindrical through holes having circular openings.

Light entrance aperture 31 and light exit aperture 32 are provided on optical axis J1 of light projector 10. In other words, light entrance aperture 31 and light exit aperture 32 are provided across from each other with detection area DA therebetween. Therefore, light that has been emitted by light projector 10, entered first reflector 30 through light entrance aperture 31, and not been scattered by particles in detection area DA continues travelling in a straight line through first reflector 30 and exits first reflector 30 through light exit aperture 32.

Moreover, first reflector 30 includes particle entrance aperture 33 for introducing into the interior of first reflector 30 particles which have entered housing 80 through inlet 80a, and particle exit aperture 34 through which particles in the interior of first reflector 30 exit first reflector 30. In other words, particle entrance aperture 33 and particle exit aperture 34 form a passage for particles (gas) inside housing 80 to pass along.

Particle entrance aperture 33 and particle exit aperture 34 are provided across from each other with detection area DA therebetween. More specifically, particle entrance aperture 33 and particle exit aperture 34 are provided along a vertically extending line (the Z axis). Particle entrance aperture 33 and particle exit aperture 34 are exemplified as, but not limited to, cylindrical through holes having circular openings.

Heater 40 is a heater that heats gas (air), such as a heater resistor. As a result of heater 40 heating gas, an upward current (a flow of gas in the positive direction along the Z axis) inside housing 80 can be generated. With this, gas dispersed with particles can be easily introduced into housing 80 via inlet 80a and guided to detection area DA.

As illustrated in FIG. 3 and FIG. 4, projection lens 50 is disposed in front of light projector 10 and transmits light (the projected beam of light) from light projector 10 toward detection area DA. Light from light projector 10 reaches detection area DA after passing through projection lens 50. Projection lens 50 is, for example, disposed 3 millimeters to 5 millimeters from light projector 10, and the focal point of projection lens 50 is located approximately 16 millimeters from light projector 10.

Projection lens 50 is, for example, a condenser that condenses (focuses) light from light projector 10 in detection area DA. In other words, the focal point of projection lens (condenser) 50 is located in detection area DA, and in this embodiment, is the same as the focal point of the ellipse defining first reflector 30. Projection lens 50 is, for example, a resin lens made of a light transmissive resin such as acrylic (PMMA) or polycarbonate (PC), or a glass lens made of glass, and has a thickness of approximately 3 millimeters and a diameter of approximately 10 millimeters.

As illustrated in FIG. 3, light attenuator 60 has a light attenuating structure (light trap structure) for attenuating light. Light attenuator 60 is a component that attenuates unwanted light (stray light) inside light attenuator 60 by reflecting the unwanted light many times. In this embodiment, light attenuator 60 attenuates light that exits first reflector 30 via light exit aperture 32. With this, light that has entered light attenuator 60 from first reflector 30 can be attenuated in light attenuator 60 to keep the light from reentering first reflector 30. Note that the shape of light attenuator 60 is determined in accordance with the internal structure formed when housing 80 (first support 81a) is resin formed.

In this embodiment, light attenuator 60 and light projector 10 are provided across from each other with detection area DA therebetween. More specifically, light attenuator 60 is an enclosed optical chamber disposed adjacent first reflector 30, and is spatially connected to first reflector 30 via light exit aperture 32 provided in first reflector 30.

Second reflector 70 is disposed on light attenuator 60. Second reflector 70 is a reflective component that reflects light that has exited though light exit aperture 32 to guide the light deep into light attenuator 60. In this embodiment, second reflector 70 is a condensing mirror that reflects light that has exited first reflector 30 through light exit aperture 32 and focuses the light on a location deep in light attenuator 60, and is, for example, a cylindrical mirror that focuses light that has exited through light exit aperture 32 into a linear beam. Second reflector 70 makes it possible to refocus, to a location deep in light attenuator 60, stray light (unwanted light) from light projector 10 that has entered light attenuator 60, which makes it possible to inhibit light that has entered light attenuator 60 from returning to first reflector 30.

Housing 80 is a case that houses, for example, light projector 10, light receiver 20, first reflector 30, heater 40, and projection lens 50. More specifically, housing 80 is configured to retain, for example, light projector 10, light receiver 20, first reflector 30, heater 40, and projection lens 50. Housing 80 is a low profile, cuboid box-like case.

As illustrated in FIG. 1 and FIG. 3, housing 80 includes inlet 80a and outlet 80b. Gas dispersed with particles enters the interior of housing 80 through inlet 80a, passes through detection area DA, and exits housing 80 through outlet 80b. Inlet 80a is an air entrance aperture for introducing air into the interior of housing 80. Outlet 80b is an air exit aperture for expelling gas out of housing 80. Note that by designing the opening of inlet 80a to be larger in area than the opening of outlet 80b, air can efficiently be introduced into and expelled from housing 80.

As illustrated in FIG. 1, housing 80 includes first housing 81 and second housing 82. Moreover, as illustrated in FIG. 2 and FIG. 3, first housing 81 includes first support 81a and second support 81b.

First support 81a supports at least light receiver 20. In this embodiment, first support 81a supports light receiver 20, first reflector 30, heater 40, and projection lens 50. In other words, projection lens 50 is supported by a component other than second support 81b. More specifically, projection lens 50 is supported by first support 81a. Second support 81b supports light projector 10.

The linear expansion coefficient of first support 81a and the linear expansion coefficient of second support 81b are different. In this embodiment, the linear expansion coefficient of first support 81a is greater than the linear expansion coefficient of second support 81b. More specifically, first support 81a is made of a resin material, and second support 81b is made of a metal material. For example, first support 81a is made of a black colored ABS resin, and second support 81b is made of aluminum. Moreover, second housing 82 is made of the same resin material as first support 81a. More specifically, second housing 82 is made of a black colored ABS resin. Note that the materials of first housing 81 (first support 81a and second support 81b) and second housing 82 are not limited to the above examples.

As illustrated in FIG. 4 and FIG. 5, first support 81a includes first placement region 81a1 in which light receiver 20 is disposed, and second placement region 81a2 in which second support 81b is disposed. For example, first placement region 81a1 is a placement surface on which light receiver 20 is placed, and second placement region 81a2 is a placement surface on which second support 81b is placed. First placement region 81a1 and second placement region 81a2 are located at different distances from optical axis J1 of light projector 10. In this embodiment, in a state in which light projector 10 is not emitting light (non light emitting state), a distance between first placement region 81a1 and optical axis J1 of light projector 10 is greater than a distance between second placement region 81a2 and optical axis J1 of light projector 10.

Moreover, first support 81a and second support 81b are connected together in a plurality of locations. First support 81a and second support 81b are fixed together by two screws 91 and 92 in a state in which first support 81a and second support 81b are in surface-to-surface contact with each other.

In particle sensor 1 configured as described above, particles dispersed in a gas (air) introduced into the interior of particle sensor 1 (housing 80) can be detected by, for example, the following.

Gas introduced into the interior of housing 80 through inlet 80a is guided to detection area DA. Here, when particles are (aerosol is) dispersed in the gas, the light from light projector 10 reflects off the particles present in detection area DA. This produces scattered light. A portion of the light scattered by the particles is reflected by first reflector 30 and guided to light receiver 20. Light incident on light receiver 20 is converted into an electric signal and output. The electric signal indicates whether or not particles are present in the gas introduced into particle sensor 1.

Moreover, it is possible to determine the size (diameter) of the particles from the size of the signal received at light receiver 20—that is to say, from the intensity of the light scattered by the particles. Thus, it is possible to determine whether the particles dispersed in the air are dust, pollen, smoke, or PM2.5 (fine particulate latter) particles.

Furthermore, since each output of the signal detected by light receiver 20—in other words, each peak intensity of light scattered by the particles—corresponds to one particle, the number of particles in the gas introduced into particle sensor 1 and the particle concentration can be calculated.

However, when the air introduced into particle sensor 1 does not include any particles, there are no particles present in detection area DA, so the light from light projector 10 passes directly through detection area DA without being scattered by particles. Thus, in this case, there is typically no response by light receiver 20, and therefore it is determined that there are no particles present in the gas introduced into particle sensor 1.

Figure 7:
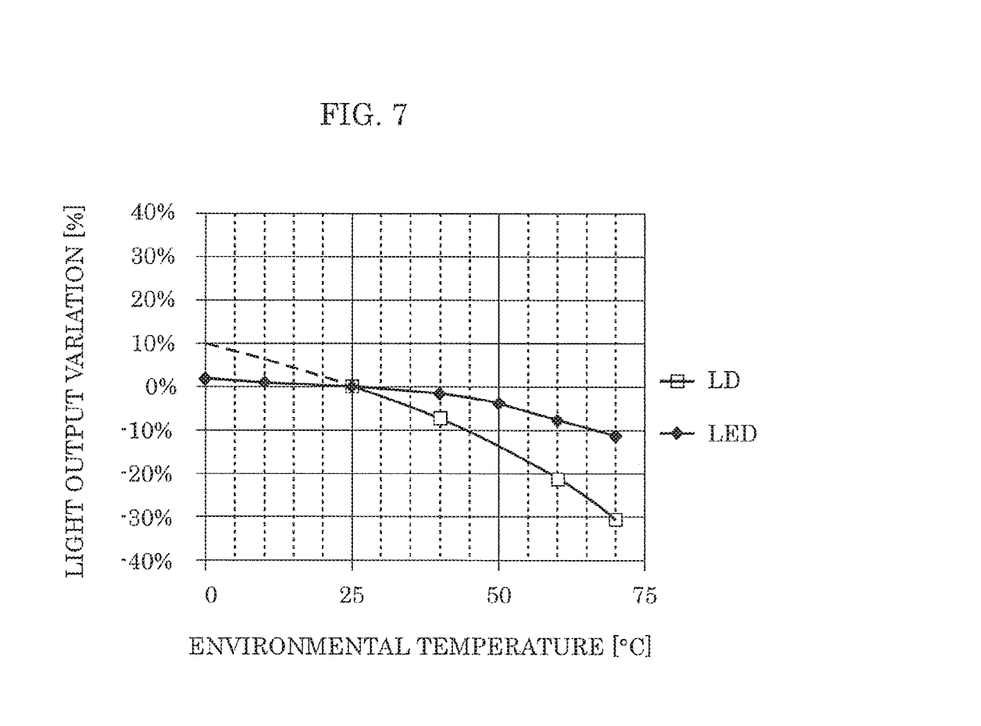
FIG. 7 illustrates the relationship between temperature and output variation in a semiconductor light emitter.
Figure 8:
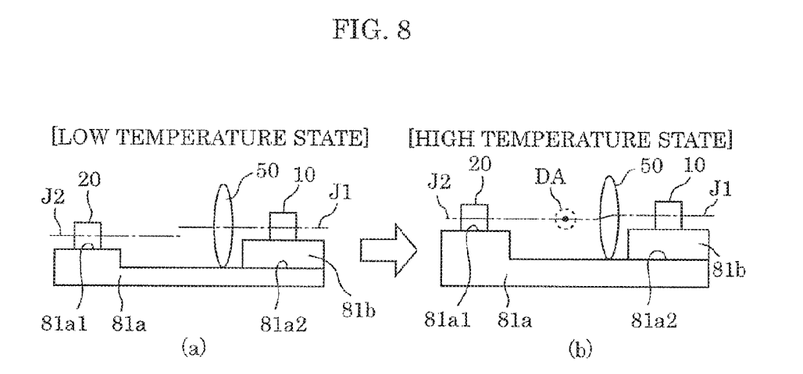
FIG. 8 is for illustrating the operating principles of the particle sensor according to the embodiment (schematically illustrates a simplified depiction of the particle sensor according to the embodiment)
Figure 9:
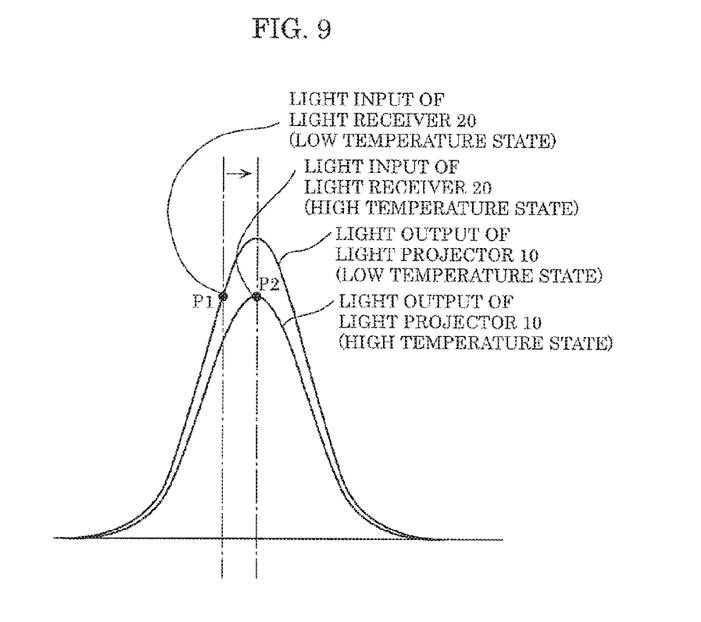
FIG. 9 is for illustrating the operating principles of the particle sensor according to the embodiment (illustrates intensity distributions of the light emitted by the light projector when the light projector is in low and high temperature states)

Next, optical operations performed by particle sensor 1 according to this embodiment will be described with reference to FIG. 7 through FIG. 9. FIG. 7 illustrates the relationship between temperature and output variation in a semiconductor light emitter. FIG. 8 schematically illustrates a simplified depiction of particle sensor 1 illustrated in FIG. 1 through FIG. 5, and is for illustrating the operating principles of particle sensor 1 according to this embodiment. FIG. 9 illustrates intensity distributions of the light emitted by light projector 10 when light projector 10 is in low and high temperature states to illustrate the operating principles of particle sensor 1.

As illustrated in FIG. 7, a semiconductor light emitter, such as an LD (semiconductor laser) or LED, itself generates heat as a result of emitting light. This increases the temperature and reduces light output of the semiconductor light emitter.

As such, with a particle sensor using a semiconductor light emitter as the light projector, the light output of the light projector decreases with use of the particle sensor. Thus, if the changes in light output caused by changes in temperature of the light projector are not corrected for, detection accuracy will decrease with the elapse of time due to the emission of light by the light projector, resulting in variations in detection accuracy.

In light of this, with particle sensor 1 according to this embodiment, since the magnitude relationship between the linear expansion coefficient for first support 81a and second support 81b, and the locations of optical axis J1 of light projector 10 and optical axis J2 of light receiver 20 are adjusted for and set in advance, changes in light output caused by changes in the temperature of light projector 10 are corrected for.

More specifically, in particle sensor 1 according to this embodiment, first support 81a is configured such that first support 81a and second support 81b have different linear expansion coefficients and, in a low temperature state (in a state in which light projector 10 is not emitting light), the distance from optical axis J1 of light projector 10 to first placement region 81a1 and the distance from optical axis J1 of light projector 10 to second placement region 81a2 are different.

In this embodiment, first support 81a is configured such that the linear expansion coefficient of first support 81a is greater than the linear expansion coefficient of second support 81b, and as illustrated in (a) in FIG. 8, in a low temperature state, which is the non light emitting state of light projector 10, the distance between first placement region 81a1 and optical axis J1 of light projector 10 is greater than the distance between second placement region 81a2 and optical axis J1 of light projector 10. In this case, in the low temperature state, optical axis J1 of light projector 10 and optical axis J2 of light receiver 20 are not optically aligned.

With this, as illustrated in (b) in FIG. 8, in the high temperature state (in a state in which, for example, particle sensor 1 is operating and, for example, light projector 10 is emitting light), since first support 81a has a higher linear expansion amount than second support 81b due to the above-described linear expansion coefficient relationship, optical axis J2 of light receiver 20 on first placement region 81a1 and optical axis J1 of light projector 10 on second placement region 81a2 become closer to each other. As a result, optical axis J1 of light projector 10 and optical axis J2 of light receiver 20 are optically aligned. In other words, optical axis J1 of light projector 10 and optical axis J2 of light receiver 20 are continuous through projection lens 50.

Here, since optical axis J1 of light projector 10 and optical axis J2 of light receiver 20 are misaligned in the low temperature state, the light input of light receiver 20 in the low temperature state is a result of scattered light having an intensity at point P1 in the light intensity distribution indicating the light output of light projector 10 in the low temperature state, as illustrated in FIG. 9. In other words, in the low temperature state, light receiver 20 receives not peak intensity light, but scattered light whose intensity is lower than the peak intensity of light emitted by light projector 10.

However, as illustrated in FIG. 9, in the high temperature state, the light output of light projector 10 decreases due to the temperature characteristics of light projector 10, but since optical axis J2 of light receiver 20 and optical axis J1 of light projector 10 become closer to each other, light receiver 20 receives scattered light generated from light output at an intensity (point P2) close to the peak intensity of the light emitted by light projector 10. In other words, optical axis J2 of light receiver 20 and optical axis J1 of light projector 10 are set to come closer to each other and optically align in the high temperature state.

As a result, as illustrated in FIG. 9, in both low and high temperature states, light receiver 20 receives scattered light generated from light of approximately the same intensity as the light emitted by light projector 10.

In this way, with particle sensor 1 according to this embodiment, in the low temperature state, particles are purposely detected without using peak intensity light from light projector 10. With this, although detection accuracy is slightly sacrificed, since scattered light generated from peak intensity light is not used in the low temperature state and scattered light generated from light having approximately the same intensity in both the low temperature state and the high temperature state is used, it possible to diminish the difference between the detection accuracy in the low temperature state and the detection accuracy in the high temperature state. In other words, it is possible to reduce variations in detection accuracy between low and high temperature states.

With particle sensor 1 according to this embodiment, since the magnitude relationship between the linear expansion coefficient for first support 81a and second support 81b and the locations of optical axis J1 of light projector 10 and optical axis J2 of light receiver 20 are adjusted for and set in advance, changes in light output caused by changes in the temperature of light projector 10 are corrected for without the use of a temperature sensor. Thus, variations in detection accuracy resulting from changes in light output caused by changes in temperature of light projector 10 can be inhibited at low cost. In other words, the detection accuracy of light projector 10 can be made to be independent of the temperature of light projector 10, and a particle sensor that is capable of maintaining a constant degree of detection accuracy can be achieved.

Figure 10:
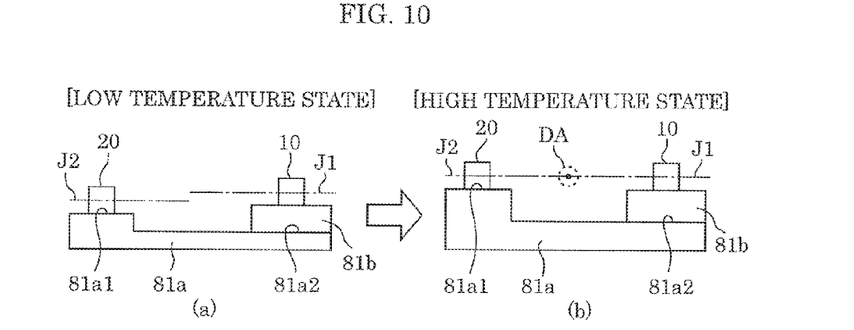
FIG. 10 is for illustrating the operating principles of a particle sensor according to according to comparative example 1 (schematically illustrates a simplified depiction of the particle sensor according to comparative example 1)

Note that projection lens 50 is used in particle sensor 1 according to this embodiment, but as illustrated in (a) and (b) in FIG. 10, it is possible to correct for changes in light output caused by changes in temperature of light projector 10 without the use of projection lens 50.

In this case, similar to (a) in FIG. 8, first support 81a is configured such that the linear expansion coefficient of first support 81a is greater than the linear expansion coefficient of second support 81b, and, as illustrated in (a) in FIG. 10, in the low temperature state, the distance between first placement region 81a1 and optical axis J1 of light projector 10 is greater than the distance between second placement; region 81a2 and optical axis J1 of light projector 10, but since projection lens 50 is not used, first support 81a and second support 81b are configured such that in the high temperature state, optical axis J1 of light projector 10 and optical axis J2 of light receiver 20 are optically aligned without the use of projection lens 50, as illustrated in (b) in FIG. 10.

As a result, similar to above, in both low and high temperature states, the scattered light received by light receiver 20 is generated from light of approximately the same intensity as the light emitted by light projector 10. Thus, since changes in light output caused by changes in temperature of light projector 10 can be corrected for without the use of a temperature sensor, variations in detection accuracy resulting from changes in light output caused by changes in temperature of light projector 10 can be inhibited at low cost.

Moreover, like particle sensor 1 according to this embodiment, first support 81a and second support 81b may be connected together in a plurality of locations. For example, like particle sensor 1 according to this embodiment, first support 81a and second support 81b may be connected together by screws 91 and 92. Such a particle sensor can be schematically represented as illustrated in (a) and (b) in FIG. 11.

Figure 11:
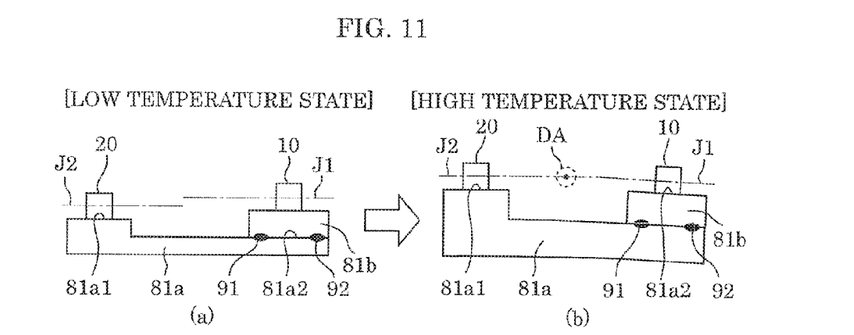
FIG. 11 is for illustrating the operating principles of the particle sensor according to comparative example 2 (schematically illustrates a simplified depiction of the particle sensor according to comparative example 2)

In this way, connecting first support 81a and second support 81b together in a plurality of locations causes second support 81b to bend in the high temperature state, as illustrated in (b) in FIG. 11. As a result, since the angle of optical axis J1 of light projector 10 can be changed, even if there is a slight change in linear expansion amount or position of second support 81b, the misalignment between optical axis J1 of light projector 10 and optical axis J2 of light receiver 20 can be increased. Therefore, even when the structure of second support 81b is small, changes in light output caused by changes in temperature of light projector 10 can be effectively corrected for.

Note that first support 81a and second support 81b may be directly or indirectly connected together. Moreover, although the particle sensor illustrated in (a) and (b) in FIG. 11 is not exemplified as including projection lens 50, the particle sensor may include and perform the adjustment with projection lens 50.

Moreover, in particle sensor 1 according to this embodiment, projection lens 50 is supported by a component other than second support 81b. More specifically, projection lens 50 is supported by first support 81a.

With this, positions of light projector 10 and the focal point of projection lens 50 can be changed. As a result, since the angle of optical axis J1 of light projector 10 can be changed, as described above, even if there is a slight change in linear expansion amount or position of second support 81b, the misalignment between optical axis J1 of light projector 10 and optical axis J2 of light receiver 20 can be increased. Therefore, even when the structure of second support 81b is small, changes in light output caused by changes in temperature of light projector 10 can be effectively corrected for.

Variation

Hereinbefore the particle sensor according to the present disclosure has been described based on an embodiment, but the present disclosure is not limited to the above embodiment.

For example, in the above embodiment, first support 81a is configured such that the linear expansion coefficient of first support 81a is greater than the linear expansion coefficient of second support 81b, and in a low temperature state, the distance between first placement region 81a1 and optical axis J1 of light projector 10 is greater than the distance between second placement region 81a2 and optical axis J1 of light projector 10, but this example is not limiting.

Figure 12:
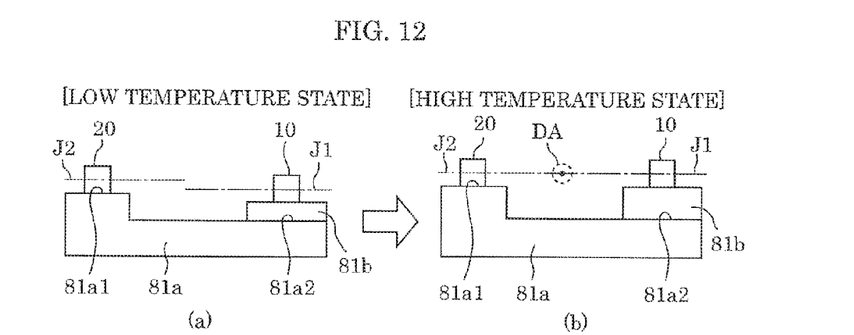
FIG. 12 is for illustrating the operating principles of a particle sensor according to comparative example 3 (schematically illustrates a simplified depiction of the particle sensor according to comparative example 3).

More specifically, first support 81a may be configured such that the linear expansion coefficient of first support 81a is less than the linear expansion coefficient of second support 81b, and, as illustrated in (a) in FIG. 12, in a low temperature state, the distance between first placement region 81a1 and optical axis J1 of light projector 10 is less than the distance between second placement region 81a2 and optical axis J1 of light projector 10.

With this, as illustrated in (b) in FIG. 12, in the high temperature state, since second support 81b has a higher linear expansion amount than first support 81a due to the above-described linear expansion coefficient relationship, optical axis J1 of light projector 10 on second placement region 81a2 and optical axis J2 of light receiver 20 on first placement region 81a1 become closer to each other. As a result, optical axis J1 of light projector 10 and optical axis J2 of light receiver 20 are optically aligned.

Therefore, due to the operating principles as described in FIG. 9, in both low and high temperature states, the scattered light received by light receiver 20 is generated from light of approximately the same intensity as the light emitted by light projector 10. Accordingly, even with the embodiments illustrated in (a) and (b) in FIG. 12, changes in light output caused by changes in the temperature of light projector 10 can be corrected for without the use of a temperature sensor. Thus, variations in detection accuracy resulting from changes in light output caused by changes in temperature of light projector 10 can be inhibited at low cost.

Moreover, in the above embodiment, first support 81a is configured such that, using optical axis J1 of light projector 10 as a reference, in a low temperature state, the distance from optical axis J1 of light projector 10 to first placement region 81a1 and the distance from optical axis J1 of light projector 10 to second placement region 81a2 are different, but this example is not limiting.

More specifically, first support 81a may be configured such that, using optical axis J2 of light receiver 20 as a reference, in a low temperature state, the distance from optical axis J2 of light receiver 20 to first placement region 81a1 and the distance from optical axis J2 of light receiver 20 to second placement region 81a2 are different. This configuration achieves the same advantageous effects as the above embodiment.

Moreover, the particle sensor according to the above embodiment can be installed in a dust sensor. For example, when the dust sensor detects dust particles via the internal particle sensor, the detection of dust is notified via sound or light or displayed on a display.

Moreover, the particle sensor according to the above embodiment can be installed in a smoke detector. For example, when the smoke detector detects smoke particles via the internal particle sensor, the detection of smoke is notified via sound or light or displayed on a display.

Moreover, the particle sensor according to the above embodiment or the above dust sensor can be installed in an air purifier, ventilation fan, or air conditioner, for example. In such a case, when the air purifier, ventilation fan, or air conditioner detects dust via the internal particle sensor, simply the fact that dust has been detected may be displayed on the display, and the fan may be controlled, such as turning on a fan or changing the rotational speed of the fan.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A particle sensor, comprising:
   a light projector that projects light to a detection area;
   a light receiver that receives scattered light, the scattered light being light from the light projector that has been scattered by particles in the detection area;
   a first support that supports the light receiver; and
   a second support that supports the light projector and has a linear expansion coefficient different from a linear expansion coefficient of the first support,
   wherein the first support includes a first placement region in which the light receiver is disposed and a second placement region in which the second support is disposed, and
   the first placement region and the second placement region are located at different distances from at least one of an optical axis of the light projector and an optical axis of the light receiver.

2. The particle sensor according to claim 1, wherein
   the linear expansion coefficient of the first support is greater than the linear expansion coefficient of the second support, and
   in a state in which the light projector is not emitting light, a distance between the first placement region and the optical axis of the light projector is greater than a distance between the second placement region and the optical axis of the light projector.

3. The particle sensor according to claim 2, wherein
   in the state in which the light projector is not emitting light, the optical axis of the light projector and the optical axis of the light receiver are not optically aligned.

4. The particle sensor according to claim 3, wherein
   the first support and the second support are configured such that, in a state in which the light projector is emitting light, the optical axis of the light projector and the optical axis of the light receiver become optically aligned.

5. The particle sensor according to claim 4, further comprising:
   a projection lens disposed in front of the light projector,
   wherein the first support and the second support are configured such that, in the state in which the light projector is emitting light, the optical axis of the light projector and the optical axis of the light receiver are continuous through the projection lens.

6. The particle sensor according to claim 1, wherein
   the linear expansion coefficient of the first support is less than the linear expansion coefficient of the second support, and
   in a state in which the light projector is not emitting light, a distance between the first placement region and the optical axis of the light projector is less than a distance between the second placement region and the optical axis of the light projector.

7. The particle sensor according to claim 6, wherein
   in the state in which the light projector is not emitting light, the optical axis of the light projector and the optical axis of the light receiver are not optically aligned.

8. The particle sensor according to claim 7, wherein the first support and the second support are configured such that, in a state in which the light projector is emitting light, the optical axis of the light projector and the optical axis of the light receiver become optically aligned.

9. The particle sensor according to claim 1, wherein the first support and the second support are at least one of directly and indirectly connected in a plurality of locations.

10. The particle sensor according to claim 1, further comprising:
a projection lens that focuses light from the light projector in the detection area,
wherein the projection lens is supported by a component other than the second support.

11. The particle sensor according to claim 10, wherein the projection lens is supported by the first support.

12. The particle sensor according to claim 1, wherein an intensity distribution in any given cross section of the light emitted by the light projector is a Gaussian distribution.

13. The particle sensor according to claim 1, wherein the optical axis of the light projector and the optical axis of the light receiver are optically misaligned, and
the first support and the second support are configured such that, in a second state different than a first state in which the optical axis of the light projector and the optical axis of the light receiver are optically misaligned, the optical axis of the light projector and the optical axis of the light receiver become optically aligned.

14. The particle sensor according to claim 1, further comprising:
a first housing including the first support and the second support; and
a second housing that is disposed opposite the first housing to define a housing in which the light projector and the light receiver are housed.

15. The particle sensor according to claim 14, wherein the first support comprises a first material,
the second support comprises a second material different than the first material, and
the second housing comprises the first material.

16. The particle sensor according to claim 1, wherein the first support comprises a resin material, and the second support comprises a metal material.

17. The particle sensor according to claim 1, wherein the light projector includes a light emitting diode or a laser diode, and
the light receiver includes a photodetector.

18. A method for detecting particles with a particle sensor, the particle sensor including a light projector, a light receiver, a first support that supports the light receiver, and a second support that supports the light projector, the method comprising:
projecting, by the light projector and in a first state, first light to a detection area, an optical axis of the light projector and an optical axis of the light receiver being optically misaligned in the first state;
receiving, by the light receiver, first scattered light, the first scattered light being light from the first light of the light projector that has been scattered by first particles in the detection area;
optically aligning, in a second state different than the first state, the optical axis of the light projector and the optical axis of the light receiver based on a linear expansion coefficient difference between the first support and the second support;
projecting, by the light projector and in the second state, second light to the detection area; and
receiving, by the light receiver, second scattered light, the second scattered light being light from the second light of the light projector that has been scattered by second particles in the detection area.

19. The method according to claim 18, wherein the light receiver receives the first scattered light at a first intensity lower than a peak intensity of the first light,
the light receiver receives the second scattered light at a second intensity closer to a peak intensity of the second light than the first intensity is to the peak intensity of the first light, and
the first intensity and the second intensity are equal.

20. The method according to claim 18, wherein the optical axis of the light projector and the optical axis of the light receiver are optically aligned based on a temperature difference between the first state and the second state.

* * * * *